United States Patent [19]
Graves et al.

[11] Patent Number: 5,920,799
[45] Date of Patent: Jul. 6, 1999

[54] METHOD FOR THE TREATMENT OF SUBSTRATES

[75] Inventors: Clinton G. Graves; Clinton G. Graves, II, both of Danville, Calif.

[73] Assignee: Graves'Trust Group, Danville, Calif.

[21] Appl. No.: 08/769,494

[22] Filed: Dec. 18, 1996

Related U.S. Application Data

[63] Continuation-in-part of application No. 08/365,666, Dec. 29, 1994, Pat. No. 5,633,424.

[51] Int. Cl.$^6$ ................................................. H01L 21/321
[52] U.S. Cl. ............................ 438/798; 438/711; 438/727
[58] Field of Search .................................. 438/7, 10, 13, 438/709, 711, 715, 725, 727, 798

[56] References Cited

U.S. PATENT DOCUMENTS

| | | | |
|---|---|---|---|
| 4,207,286 | 6/1980 | Boucher | 422/21 |
| 4,976,920 | 12/1990 | Jacob | 422/23 |
| 5,115,166 | 5/1992 | Campbell et al. | 315/111.21 |
| 5,171,525 | 12/1992 | Jacob | 422/23 |
| 5,184,046 | 2/1993 | Campbell | 315/111.21 |
| 5,200,158 | 4/1993 | Jacob | 422/292 |
| 5,213,758 | 5/1993 | Kawashima et al. | 422/21 |
| 5,223,231 | 6/1993 | Drake | 422/297 |
| 5,325,020 | 6/1994 | Campbell et al. | 315/111.21 |

*Primary Examiner*—Charles Bowers
*Assistant Examiner*—Reneé R. Berry
*Attorney, Agent, or Firm*—Townsend and Townsend and Crew

[57] ABSTRACT

The invention provides methods and apparatus for treating substrates and hazardous biological wastes. According to one exemplary method, at least one substrate is placed into a chamber and a vacuum is applied to the chamber. After the pressure within the chamber is sufficiently reduced, water vapor is introduced into the chamber and electromagnetic radiation energy is applied to produce a plasma. In one particularly preferable aspect, the chamber is allowed to reach a static condition before the water vapor is introduced. In this way, the water vapor is able to equally distribute itself throughout the volume of the chamber so that an equally distributed plasma can be produced upon application of the electromagnetic radiation energy.

16 Claims, 3 Drawing Sheets

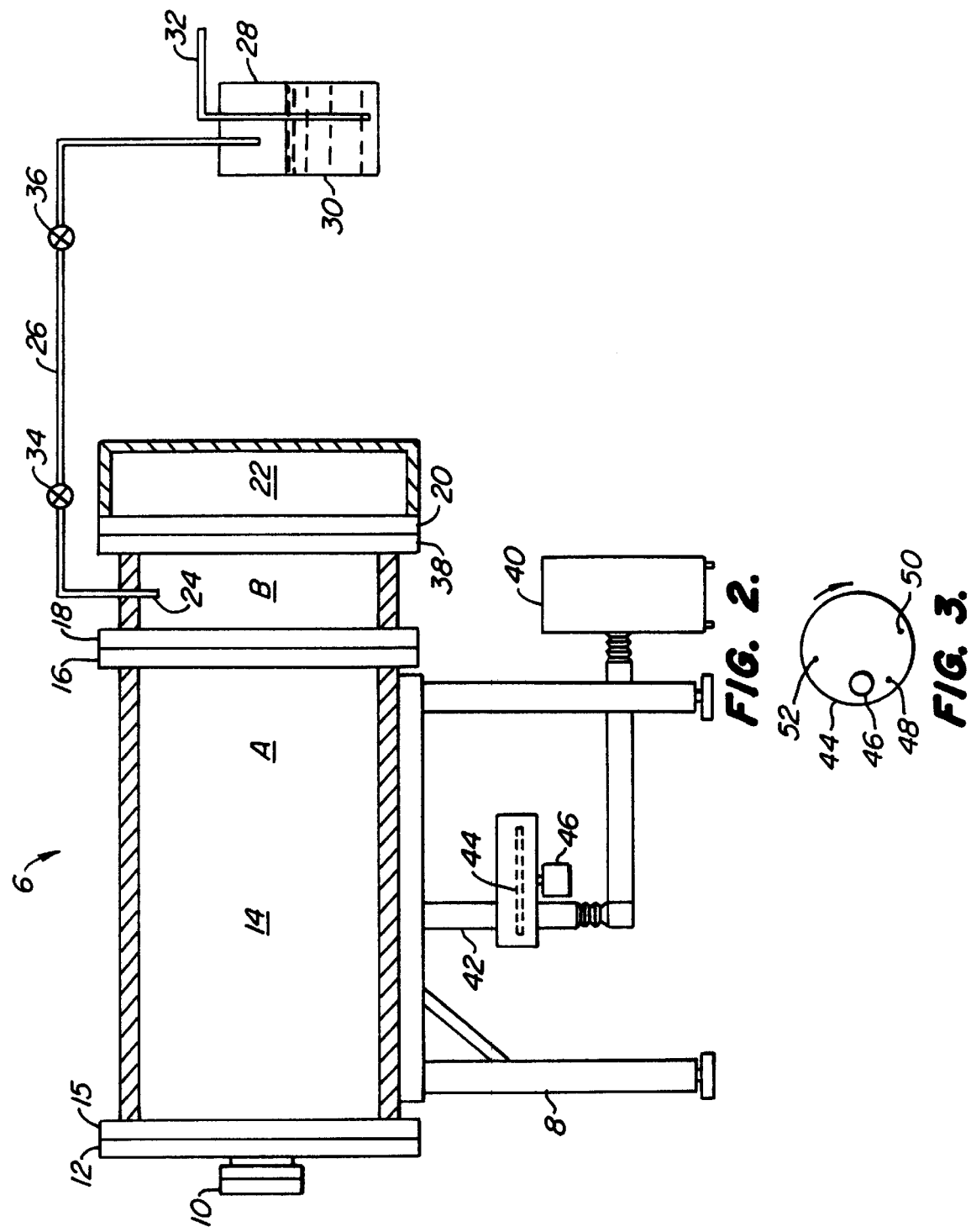

METHOD FOR THE TREATMENT OF SUBSTRATES

CROSS REFERENCE TO RELATED APPLICATIONS

This application is a continuation in part application of U.S. patent application Ser. No. 08/365,666, filed Dec. 29, 1994, now Pat. No. 5,633,424, the complete disclosure of which is herein incorporated by reference.

BACKGROUND OF THE INVENTION

1. Field of the Invention

This invention relates generally to methods and apparatus for sterilizing articles and hazardous biological waste, and for the treatment of various substrates. In particular, the invention provides methods and apparatus for sterilizing articles with a gas plasma generated from a gas mixture of oxidizing and reducing agents. Methods and apparatus are also provided for treating, e.g. stripping, cleaning, plasma treating, etching or depositing a film, various substrates with a plasma having a generally uniform density. In one particular aspect, this invention provides for the sterilization of articles with a gas plasma generated from water vapor.

A variety of sterilization methods have been proposed for sterilizing a wide range of articles such as medical products, surgical instruments, pharmaceutical products, and the like. One common method is by subjecting the articles to a gas such as ethylene oxide or other disinfecting gases. Irradiation procedures have also been proposed for sterilizing articles such as medical products.

One expectation for all sterilizing procedures is that they must effectively kill all organisms without damage to the articles or goods being sterilized. Although some sterilization procedures meet these criteria, including the use of ethylene oxide and other procedures, many sterilizers using such gases suffer from number of serious drawbacks. For example, use of such gases is often too corrosive for the articles being sterilized or their packaging materials. Another drawback is that a toxic residue usually remains on the sterilized articles. In another drawback that affects all traditional methods of sterilization, although the microorganisms are usually destroyed by the plasma, the destroyed microorganisms still physically remain on the articles.

Sterilization gas procedures and irradiation procedures often expose workers and the environment to unacceptable safety standards. Such exposure is becoming increasingly more undesirable, particularly in light of state and federal legislation restricting the use of hazardous materials.

Such restrictions are forcing hospitals and other medical facilities to search for other alternatives. One such alternative is a plasma sterilizer. Plasma sterilizers operate by injecting a gas into a chamber and applying electromagnetic radiation energy to the gas in the chamber which in turn ionizes the body of gas. The ionized gas should be highly reactive and reacts with microorganisms on the surface of the articles to be sterilized. The reactions between the ionized gas and the microorganisms should effectively destroy the microorganisms. Sterilizing plasmas have been generated with a wide variety of gases as set forth generally in U.S. patent application Ser. No. 5,184,046, the disclosure of which is herein incorporated by reference.

One drawback with using such plasma sterilizers is that it is often difficult to ensure that all of the articles in the sterilizer have been completely sterilized. Such a problem arises because of the difficulty in achieving uniform gas dynamics and uniform plasma density when the articles being sterilized are of different sizes or shapes. This problem is compounded by the use of non-cylindrical reaction chambers and differing batch sizes. The non-uniformity of the gas dynamics results in a non-uniform plasma density, which in turn provides a non-uniform plasma treatment and insufficient sterilization.

Another problem experienced in sterilizing articles is the problem of maintaining the sterility of the articles during packaging. Current sterilization techniques, such as plasma sterilization and gas sterilization, generally require. the articles to be sterilized and then subsequently packaged. To maintain sterility during packaging, the articles are packaged in a sterile environment. Such a procedure is inconvenient and expensive.

The treatment of hazardous biological waste is also of interest to the invention. Hazardous biological waste is typically collected at the point of source and is usually consolidated with other hazardous biological waste from other sources and different locations. The handling, transportation, and storage of these materials can be problematic and can require special training, handling and tracking. Furthermore, there is a high risk of accidental contamination associated with the handling and storage of such wastes.

To destroy such wastes, the wastes are usually placed in an incinerator and burned at about 3000 degrees C. The burning of the hazardous biological waste in this manner poses various problems since many of the packaging materials are constructed from plastics and release toxic gases when burned.

The treatment of various substrates, such as semiconductor and microelectronic substrates, has also proved to be difficult and challenging. Traditionally, such substrates were processed using wet chemistries. Since the substrates were relatively small and the line geometries were relatively large, non-uniformity of the chemical treatment was not generally problematic. With the demand for larger sized substrates, most manufacturers have resorted to the use of gas plasma processes. However, due to the relatively large size of the substrates, e.g. 400 mm by 400 mm or larger, such processes have proved to be generally ineffective. For example, the achievement of uniform gas dynamics and uniform plasma density within relatively large reaction chambers has been difficult, if not impossible. As a result, both substrate sizes and batch sizes have remained small. Further, such processes have generally produced low yields.

It would therefore be desirable to provide methods and apparatus to overcome or reduce such problems relating to plasma sterilization, the treatment of hazardous biological waste, and the treatment of various substrates. In particular, the methods and apparatus should provide for plasma sterilization that is not corrosive to the articles and does not leave toxic residues on the articles. The methods and apparatus should not only be able to effectively destroy the microorganisms, but also to remove them from the articles. Further, the methods and apparatus should provide for uniform plasma distribution, thereby insuring uniform sterilization regardless of the chamber geometry or the size and geometry of the articles to be sterilized. It would further be desirable to provide methods and apparatus for sterilizing articles within packaging suitable for delivery to an end user.

In the case of biological wastes, it would be desirable to treat the hazardous waste at the production site so that no special handling, transportation or storage of the waste will be required.

In another aspect, it would be desirable to provide methods and apparatus for treating various substrates, regardless of their size. Such methods and apparatus should also allow for large substrate sizes and/or batch sizes, produce good yields, and be economical.

2. Description of the Background Art

U.S. Pat. Nos. 5,115,166, 5,184,046, and 5,325,020 describe various apparatus and methods for plasma sterilization.

U.S. Pat. No. 4,207,286 describes a sterilization method using a continuous flow, low pressure gas plasma.

SUMMARY OF THE INVENTION

The invention provides methods and apparatus for sterilizing articles, for sterilizing hazardous biological waste, and for treating various substrates using a gas plasma. According to one particular sterilization method, an article or biological waste is placed into a sterilization chamber and a vacuum is applied to the chamber to reduce the pressure within the chamber. With the pressure reduced, water vapor is introduced into the chamber. The water vapor can be introduced alone or can optionally be introduced with a carrier gas. With the water vapor in the chamber, an electromagnetic radiation energy is applied to the chamber to produce a plasma. The electromagnetic radiation energy excites the water molecules and causes them to disassociate thereby creating reactive radicals. The reactive radicals vaporize and combine with the by-products of the spores and other microorganisms and to effectively destroy and remove the spores and other microorganisms from the articles or waste, thereby sterilizing the articles or waste.

In an exemplary aspect, the carrier gas comprises air. Alternatively, the carrier gas can be a gas selected from the group consisting of argon, hydrogen, oxygen, nitrogen, helium, nitrogen tri-fluoride, and nitrous oxide. The electromagnetic radiation energy applied to the chamber is preferably in the range from about 5 KHz to 10 GHz, and more preferably at about 2.45 GHz. Such a wavelength is preferable because of its effectiveness in disassociating the hydrogen and oxygen atoms of the water vapor.

When the water vapor is introduced into the chamber, the pressure within the chamber is preferably within the range from about 100 mTorr to 10 Torr. In another aspect, the temperature within the chamber is preferably in the range from about 25° C. to 100° C.

In an alternative method for sterilizing articles, at least one article is placed into a sterilization chamber and a vacuum is applied to the chamber until a predetermined pressure is reached within the chamber. Once such a pressure is reached, application of the vacuum is ceased and a static condition is allowed to develop within the chamber. Once a static condition has been reached, an amount of gas is introduced into the chamber and is allowed to uniformly distribute throughout the chamber. Because of the static condition within the chamber, pressure is equal throughout the chamber allowing the concentration of the gas to readily become uniform throughout the entire volume of the chamber. In such a state, electromagnetic radiation energy is applied to the chamber to produce a plasma.

After the plasma has had sufficient time to react with the spores and other microorganisms, the electromagnetic radiation power is ceased and any gases are exhausted from the chamber. One or more cycles can be applied. In a preferable aspect, the gas introduced into the chamber is water vapor. When water vapor is used to produce the plasma, the reactions within the chamber produce water vapor, oxygen, and nitrogen with small amounts of carbon dioxide and carbon monoxide. Such gases can be safely exhausted into the atmosphere.

After the gases are exhausted into the atmosphere, the cycle of applying a vacuum to the chamber, allowing a static condition to develop, introducing the gas into the chamber, and applying electromagnetic radiation energy are again repeated as necessary to ensure that the articles within the chamber are sufficiently sterilized.

The invention provides an apparatus that may be used to sterilize articles or hazardous biological waste, or to treat various substrates. The apparatus includes a treatment chamber and both a vacuum pump and a gas source in communication with the chamber. The vacuum pump allows the pressure within the chamber to be reduced. Once the pressure is reduced, the gas source can be employed to introduce a gas into the chamber. The apparatus further includes an electromagnetic radiation energy source to produce a plasma from the gas within the chamber. A controller is provided for cyclically actuating the vacuum pump, the gas source, and the electromagnetic radiation energy source. In a preferable aspect, the controller is configured so that the vacuum pump, the gas source, and the electromagnetic radiation energy source are actuated at separate times. In this way, the apparatus can be operated in a cyclical manner to continuously produce and exhaust a plasma. Operation in this manner allows articles to be uniformly sterilized and allows for uniform treatment of substrates.

In particular, the controller allows the vacuum pump to reduce the pressure in the chamber to a desired pressure. At this point, the controller stops the vacuum pump and allows the chamber to reach a static condition. When such a condition is reached, the controller actuates the gas source to inject an amount of gas into the chamber. Since the chamber is in a static condition, the gas equally distributes throughout the chamber. At this point, the electromagnetic radiation energy source is actuated by the controller to produce a uniformly distributed plasma within the chamber for uniformly sterilizing the articles or treating substrates. After reaction of the plasma with the microorganisms on the articles, the resulting gases are exhausted and the controller sends a signal to repeat the cycle as often as is desired.

In a preferable aspect, the vacuum pump is connected to the chamber by a tube, and the controller includes a rotatable disk having an orifice that can be aligned with the tube as the disk is rotated. In this manner, each time the orifice comes in alignment with the tube, a vacuum is created within the chamber. The rotating disk also serves as a timer to actuate the injection of the gas and the application of the electromagnetic radiation energy. A sensor can be employed for sensing the degree of rotation of the disk so that a signal can be sent to actuate the gas source or the electromagnetic radiation energy source at the appropriate times. In this way, the cycle of the apparatus is controlled by the rotation of the disk.

The invention further provides a method and apparatus for sterilizing pre-packaged articles, with the packaging being suitable for delivery to an end user. The packaging includes a container constructed of a material transparent to electromagnetic radiation energy, such as plastic. To sterilize the article, the article is placed in the container and a vacuum is applied to the chamber until a pressure in the range from about 1 mTorr to 100 mTorr is reached. The container is then back filled with water vapor to a pressure in the range from about 100 mTorr to 100 Torr. A carrier gas is used to introduce the water vapor. The container is then sealed and is subjected to electromagnetic radiation energy to form a highly energetic water vapor in the container. The electromagnetic radiation is then ceased and a static condition is allowed to develop in the container. The electromagnetic radiation energy is again reapplied until sterilization is complete. The articles then remain in a sterilized environment within the packaging until removed by the end user.

The invention still further provides an exemplary method for treating substrates. According to the method, at least one substrate is placed into a chamber and a vacuum is applied to the chamber. Application of the vacuum is then ceased and a static condition is allowed to develop in the chamber where the pressure throughout the chamber is essentially equal and constant. After the static condition has developed, an amount of gas is introduced into the chamber and allowed to uniformly distribute itself throughout the chamber. Electromagnetic radiation energy is applied to the chamber after the gas has become uniformly distributed within the chamber to produce a substantially uniformly distributed plasma within the chamber.

After this cycle is completed, application of the electromagnetic radiation energy is ceased and gases are exhausted from the chamber. If necessary, the cycle may be repeated to further treat the substrate.

In one aspect of the method, the substrate is selected from the group of substrates consisting of semiconductor substrates, microelectronic substrates, flat panel displays, transducers, and the like. In another aspect, the plasma is produced to strip, clean, etch, deposit a substance on the substrate, or the like.

In one particular advantage of the method, a plurality of substrates may be introduced into the chamber at the same time to simultaneously treat multiple substrates. Further, the method may be employed to treat large substrates which are on the order of about 400 mm by 400 mm or greater. Treatment of such relatively large substrates in large batch sizes is facilitated by removing the gas flow dynamics from the chamber while the plasma is produced. This is turn produces a substantially equally distributed plasma to uniformly treat all substrates held within the chamber, regardless of their size or arrangement. Moreover, the uniform plasma allows for high yields and therefore makes the process economically efficient.

BRIEF DESCRIPTION OF THE DRAWINGS

FIG. 2 illustrates a partially cut-away side view of a sterilization or treatment apparatus according to the present invention.

FIG. 3 illustrates a top view of a rotating chopper valve for controlling the sterilization or treatment cycle of the apparatus of FIG. 2.

DETAILED DESCRIPTION OF THE SPECIFIC EMBODIMENTS

Figure 1A:
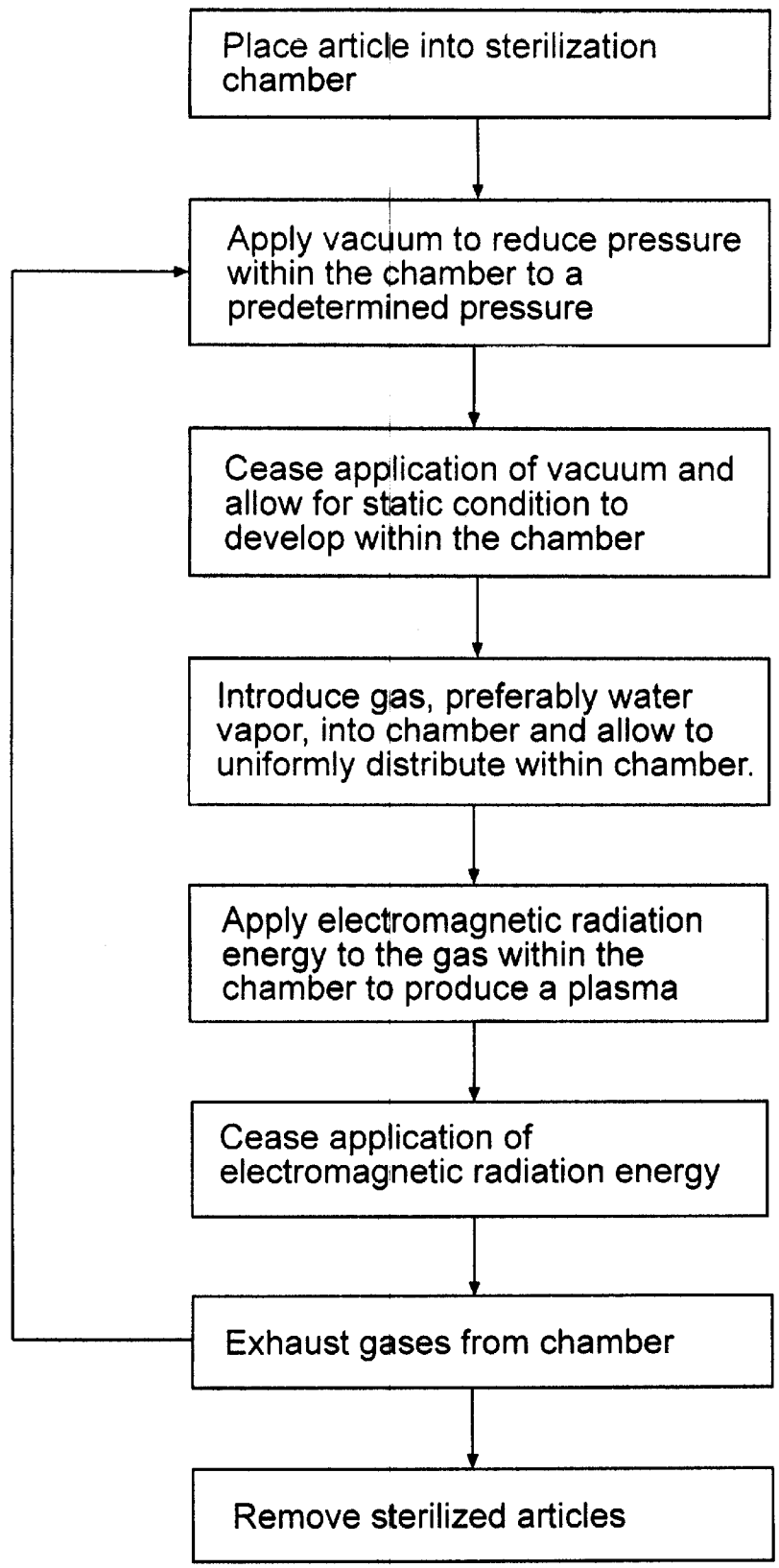
FIG. 1A is a flowchart illustrating an exemplary method for sterilizing articles using a gas plasma according to the present invention.

This invention provides methods and apparatus for sterilizing articles and hazardous biological waste, and for treating various substrates. When sterilizing articles or hazardous wastes, the invention will employ the use of a gas plasma generated from a gas mixture of oxidizing and reducing agents. In a preferable aspect, the articles are sterilized with a gas plasma that is generated from water vapor. Other gases that may be used include $O_2$, NO, $N_2O$, air, and hydrogen peroxide.

According to the method for sterilizing articles and hazardous biological wastes using a gas plasma that is created from water vapor, at least one article or an amount of waste is introduced into a sterilization chamber. The article can be selected from any of a number of articles, such as surgical instruments, dental instruments, medical products, pharmaceutical products, and the like. After the article or waste is within the chamber, a vacuum is applied to the chamber to reduce the pressure within the chamber to a pressure below atmospheric pressure. Preferably, the pressure will be reduced until it is in the range from about 100 mTorr to 10 Torr. When the pressure within the chamber is within the desired range, a water vapor is introduced into the chamber. Conveniently, the water vapor can be introduced into the chamber by a carrier gas. The carrier gas can be any one of a number of gases including such gases as air, argon, hydrogen, nitrogen, oxygen, helium, nitrogen tri-fluoride, nitrous-oxide, and the like, or any mixtures thereof. Preferably, air will be used as the carrier gas. Although such carrier gases can conveniently be used to assist in introducing the water vapor into the chamber, a novel feature of the invention is that water vapor alone can be used to produce the plasma.

Once the water vapor has been introduced into the chamber, electromagnetic radiation energy is applied to the water vapor while the pressure within the chamber is maintained in the desired range. Electromagnetic radiation energy as used herein includes all radio frequency energy and particularly any radio frequency energy having a wavelength in the range from about 5 KHz to 10 GHz, and also includes energy such as microwave, infrared light, visible light, ultraviolet light, laser, X-ray energy and gamma radiation. When the radio frequency energy is supplied, the water molecules are driven into a high energy state, causing the molecules to disassociate into reactive radicals and forming a plasma. The radio frequency energy will preferably be at about 2.45 GHz which has proven to be effective in fractionating the water molecules. The reactive radicals then vaporize and combine with the by-products of spores or other microorganisms on the articles or waste to sterilize the articles or waste. The reactions of the radicals with the spores and other microorganisms produce water vapor, oxygen, nitrogen, and small amounts of carbon dioxide and carbon monoxide. A particular advantage in using water vapor to create the plasma is that when the reactive radicals combine with the spores and other microorganisms on the articles or waste, they are effectively vaporized. In this way, the spores and other microorganisms are physically removed from the articles or waste and converted to gas form which is then exhausted from the chamber. A further advantage in using water vapor to create the plasma is that the exhausted gases, i.e., water vapor, oxygen, nitrogen, and small amounts of carbon dioxide and carbon monoxide, can be safely exhausted into the atmosphere. In still a further advantage, the temperature within the chamber during the sterilization process can be in the range from about 25° C. to 1000° C. Such temperatures provide for a safe working environment and do not impose additional costs in constructing the sterilization apparatus.

One advantage of this process is that a hazardous biological waste may be sterilized where it is created, thus requiring no special handling, transportation, or storage. Thus, the risk of accidental contamination is low. In this way, the hazardous biological waste may be rendered harmless and then moved through normal channels.

An exemplary method for uniformly sterilizing articles, including hazardous biological wastes, using a gas plasma is set forth in the flowchart of FIG. 1. According to the method, at least one article is placed into a sterilization chamber. The article can be of any size or geometry as long as it can fit within the sterilization chamber. With the article in the chamber, a vacuum is applied to the chamber to reduce the pressure to a predetermined amount. When such a pressure is reached, application of the vacuum is ceased and a static condition is allowed to develop in the chamber, i.e., a condition where the pressure remains essentially constant and equal throughout the entire interior of the chamber. Once a static condition has been reached, a discrete amount of gas is introduced into the chamber. Because of the static condition within the chamber, the gas rapidly distributes itself uniformly throughout the entire volume of the chamber as dictated by Boyle's law. This removes gas flow dynamics from the equation.

With the gas equally distributed throughout the entire interior volume of the chamber, electromagnetic radiation, and preferably radio frequency energy, is applied to the gas to produce a plasma. The gas can be any one of a number of gases capable of producing reactive radicals, but will preferably include water vapor. The radio frequency energy is applied for a time sufficient to allow the reactive radicals to react with the spores and other microorganisms on the articles. The amount of time the radio frequency energy is applied can be increased as desired to introduce a safety factor. After the plasma has had sufficient time to react, the radio frequency energy is ceased and the resultant gases are exhausted from the chamber.

Because only a discrete amount of gas is introduced at a time into the chamber, the cycle of applying a vacuum to the chamber, allowing a static condition to develop, introducing another amount of gas into the chamber, and applying radio frequency energy can again be repeated as necessary to ensure that the articles within the chamber are sufficiently sterilized.

Figure 1B:
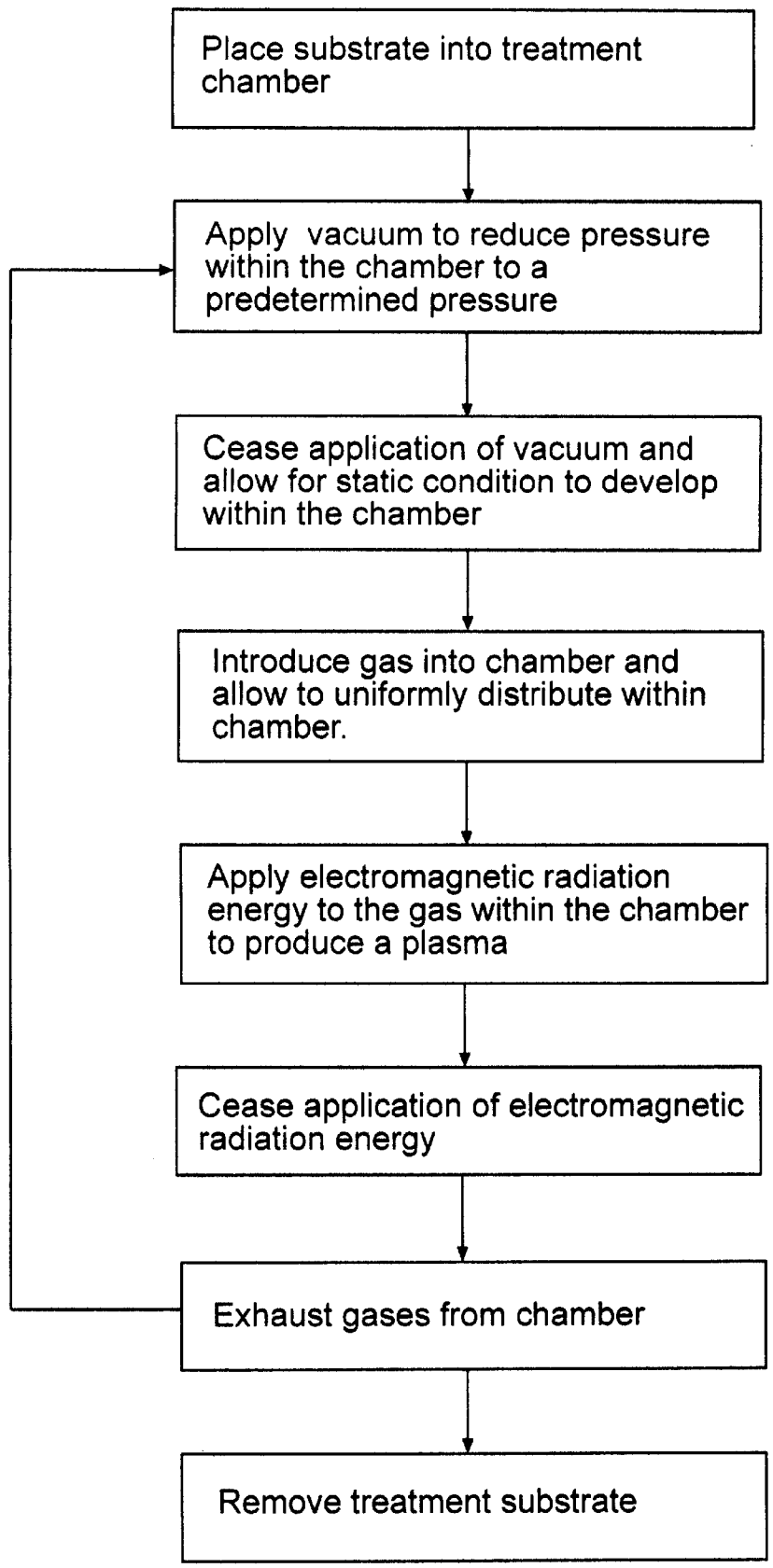
FIG. 1B is a flowchart illustrating an exemplary method for treating substrates using a gas plasma according to the present invention.

The invention further provides an exemplary method for treating various substrates, such as semiconductor substrates, microelectronic substrates, flat panel displays, transducers, and the like. The treatments contemplated by the invention include stripping, cleaning, plasma treating, etching, receiving of a deposition film, and the like. The treatment of the various substrates is similar to the sterilization process previously described and is illustrated in FIG. 1B.

As shown, substrates are treated by placing one or more substrates into a treatment chamber. A vacuum is then applied to the chamber to reduce the pressure to a predetermined amount. At this point, application of the vacuum is ceased and a static condition is allowed to develop within the chamber at the reduced pressure. While at the static condition, a gas or gas mixture is introduced into the chamber and allowed to uniformly distribute itself within the chamber. At this point, electromagnetic radiation energy is applied to the gas within the chamber to produce a plasma. After a specified time, application of the electromagnetic radiation energy is ceased and gasses are exhausted from the chamber. To sufficiently treat the substrate, the cycle may be repeated as many times as needed.

One particular advantage of such a method is that the gas is injected into a static reaction chamber volume. Under such conditions, the pressure is equalized and the concentration of gasses is uniform throughout the entire volume of the chamber. By providing a uniform gas distribution, a uniform plasma treatment may be provided by applying electromagnetic radiation energy to the gas.

Application of the electromagnetic radiation drives the gas molecules into a high energy state causing them to fractionate to create reactive radicals. The reactive gasses are then used to treat the substrates.

Such a method for treating the substrates is further advantageous in that relatively large substrates may be uniformly treated. Since no gas flow dynamics exist within the chamber, every point of the substrate within the chamber will experience approximately the same plasma treatment. In this manner, the size of substrate is limited only by the size of the chamber. For example, substrates that are 400 mm by 400 mm or greater may be uniformly treated. Similarly, the batch size is limited only by the size of the chamber. In this manner, multiple substrates may be treated simultaneously, with each substrate being uniformly treated. In a further advantage, since the plasma density is uniform in the reaction chamber, high yields are possible, therefore making the treatment of substrates extremely efficient.

The types of gasses introduced into the chamber will vary depending upon the particular treatment. For example, various substrates may be subjected to a reactive ion etching process using $CF_4$, $CHF_3$, $NF_3$, $SF_6$, $CCl_2F_2$, $CCl_4$, $SiCl_4$, $Bcl_3$, $HCl$, $HBr$, $Clr$, $CF_8$, and the like. These gases may be used individually or in combination, and with or without the presence of $O_2$, $NO$, $N_2O$, $H_2O$ or $O_3$. Such gasses are particularly useful when etching oxides, nitrides, silicons, polysilicons, polyamide and the like. The process may also be employed to etch various metals, such as aluminum, nickel, gold, and the like. Exemplary gasses for etching such metals include $CL_2$, $CCL_4$, $SiCL_4$ $BCL_3$, and other chlorine-bearing gasses including $CCL_2F_2$.

Exemplary gasses for photoresist stripping processes for wafers or other substrates include water vapor, $O_2$, $NO$, $N_2O$, air, $H_2$, $N_2$, $Hl$, $Ar$, and the like, alone or in combination. Exemplary gasses for depositing a film include $SiH_4$, $NH_3$, $N_2O$, $NO$, $Ar$, $SiO_2$, $Si_3N_4$, and $Si$.

When treating the various substrates, the reaction chamber will preferably be evacuated to a pressure in the range from about 1 mTorr to about 10 Torr. Preferable ranges for the applied electromagnetic radiation energy will be in the range from about 5 KHz to about 10 GHz.

Referring to FIG. 2, an exemplary embodiment of an apparatus 6 that may be employed to sterilize articles as set forth in FIG. 1A or to treat various substrates as set forth in FIG. 1B will be described. The apparatus 6 is conveniently placed on a table 8 for easier access. The apparatus 6 includes a view port 10 within a door 12. The door 12 is connected to a reaction chamber 14 via a flange 15. Visual access to the reaction chamber 14 is obtained through the view port 10, while physical access is gained by opening the door 12. Preferably, the door 12 will be hingedly connected to the flange 15. The door 12, the flange 15, and the chamber 14 will preferably all be constructed of stainless steel. Use of stainless steel for these components is advantageous because the stainless steel does not sputter (i.e., the physical deposition of material on substrates) as would aluminum or aluminum oxide, causing damage and contamination to the articles being sterilized or to the substrates.

Attached to an opposite end of the reaction chamber 14 is another stainless steel flange 38. The flange 38 is used to attach a material transparent to radio frequency energy, such as a glass or quartz plate seal 20 through which radio frequency energy is directed.

To inject gas into the reaction chamber 14, a gas injection port 24 is provided. Gas is supplied to the injection port 24 through a gas line 26. In turn, the gas line 26 is in communication with a gas source 28. The gas source 28 can be configured to provide any one of a variety of gases, and will preferably be configured to provide water vapor as the gas. To provide the water vapor, the gas source 28 includes a container 30 having an amount of water $H_2O$. Placed in the water is a carrier gas delivery tube 32 for bubbling a carrier gas through the water. In this way, as the carrier gas is bubbled through the water, water vapor is produced which can be delivered to the reaction chamber 14 through the gas line 26. A gas injection valve 34 is provided for controlling injection of the gas into the reaction chamber 14. A gas metering valve 36 is provided to meter the amount of gas travelling through the gas line 26.

Although shown with only a single gas injection port 24, the apparatus 6 can alternatively be provided with a plurality of gas injection ports disposed throughout the reaction chamber 14. In such a configuration, a header can be provided to distribute the gas to the various gas injection ports around the reaction chamber 14.

A radio frequency energy source 22 is provided for supplying radio frequency energy into the chamber at a wavelength in the range from about 5 KHz to 10 GHz. Preferably, the radio frequency energy supplied by the generator source 22 will be at about 2.45 GHz for the sterilization process. Such a wavelength is the same wavelength produced by most commercially available microwave ovens. Conveniently, the generator source 22 can be constructed from the power supply of a commercially available microwave oven. The radio frequency energy is directed through the plate seal 20 and into the reaction chamber 14. As previously described, the plate seal 20 is constructed of a material transparent to radio frequency energy, and is preferably constructed of a glass or a quartz plate. The stainless steel flange 38 is provided to attach the generator source 22 to the reaction chamber 14.

The gas injected into the reaction chamber 14 is allowed to equally distribute itself throughout the entire interior volume of the reaction chamber 14. This is accomplished by sealing the chamber 14 after the gas is injected. When the gas is within the reaction chamber 14, the radio frequency generator source 22 can be actuated to direct energy through the plate seal 20 and into the reaction chamber 14. In this way, a plasma is produced when the gas is energized by the radio frequency energy.

In some instances, it may be desirable to provide a diffuser plate 18. The diffuser plate 18 is held by a flange 16 and divides the reaction chamber 14 into two separate volumes. The volume adjacent the door 12 (volume A) is for holding the articles and the volume adjacent the generator source 22 (volume B) is for receiving the injected gas. The diffuser plate 18 contains at least one through hole so that the two volumes A, B can communicate. More than one through hole can be included for multiple point injection of the gas. As gas is injected into volume B adjacent the radio frequency generator source 22, this volume is immediately filled with gas. Volume A is also almost immediately filled with the gas through the through hole. The rate at which volume A is filled can be varied depending on the pressure difference between the volumes A, B and the size and quantity of through holes.

At this point, it is possible to produce a plasma in volume B, but not in volume A. As described hereinafter, plasma can alternatively be produced in both volume A and B in any proportion so that the articles in volume A can be exposed only to the reactive gases, or to any combination of reactive gases and ionic bombardment. To produce the plasma only in volume B, a metallic cover is placed adjacent the plate 18 (or substituted for plate 18) to prevent radiation energy from entering volume A when the radio frequency generator 22 is actuated to produce a plasma in volume B. In this way, the articles in volume A receive no ionic bombardment and are only exposed to the previously diffused reactive gases in volume A. This procedure is particularly beneficial when sterilizing sensitive articles such as cameras, microscopes, optics, implantable sensors, lenses, and the like.

To sterilize without ionic bombardment over a broader range of parameters, a second metal gas diffusion plate with one or more through holes can be rotatably received relative to the first plate. As the second plate is rotated relative to the first plate, the through holes come in and out of alignment allowing for varying degrees of gas diffusion into volume A.

The radio frequency generator source 22 can be actuated at different times relative to the injection of the gas into the volume B to vary the amount of plasma diffused into the volume A. If the radio frequency energy is actuated just as the gas is injected into the volume B, then a plasma will be created that can then be diffused into the volume A. If the generator source 22 is actuated well after the gas has diffused into the volume A, then virtually no plasma will be diffused into the volume A.

In some circumstances, particularly when using low frequency electromagnetic radiation energy, it may be difficult to couple the electromagnetic radiation energy through the plate seal 20. In such a case, the electromagnetic radiation energy can be inductively or capacity coupled through the glass or quartz plate 20 into the reaction chamber. To capacity couple the energy source, an electrode can be employed and placed either inside or outside the reaction chamber 14. Use of the electrode inside the chamber 14 is useful when using electromagnetic radiation energy having a frequency of 10 MHz or less. Use of the electrodes outside the chamber is useful when using electromagnetic radiation energy having frequencies in the range from 10 MHz to 900 MHz. To inductively couple, a copper tube, preferably having a diameter in the range from $3/16$" to $1/4$" is arranged on the outside surface of the plate 20. Energy is supplied through the wire at a frequency in the range of about 10 MHz to 900 MHz and is coupled through the plate 20 to produce the plasma.

The reaction chamber 14 can be constructed of any geometry, but will preferably be orthogonal or cylindrical in geometry. An orthogonal geometry is advantageous when using trays to carry the articles to be sterilized. Use of trays allows for easy arrangement of the articles within the chamber 14.

To reduce the pressure within the reaction chamber 14 prior to injection of the gas, a vacuum pump 40 is provided. The vacuum pump 40 can be any pump capable of reducing pressures within the reaction chamber 14 up to a pressure of about 10 mTorr. An exemplary vacuum pump 40 is one such as the Alcatel 1220, commercially available from Alcatel. The vacuum pump 40 also serves to exhaust gases from the reaction chamber 14 after sterilization or other treatment has occurred. The vacuum pump 40 communicates with the reaction chamber 14 via an exhaust port 42.

As previously described in the methods of the invention, it is desirable to provide a uniformly distributed plasma within the chamber 14 regardless of the geometry of the reaction chamber 14 or the articles or substrates themselves.

To provide a uniform plasma treatment, a static condition is created within the chamber 14 by ceasing the pumping. A discrete amount of gas, i.e., a known volume, can be injected into the reaction chamber 14 through the port 24 which is then closed. The gas is then allowed to equally distribute itself throughout the entire interior volume of the reaction chamber 14. Radio frequency energy from the generator source 22 is directed into the chamber 14 to create a uniform plasma, thereby allowing for uniform sterilization or treatment of the articles or substrates regardless of their size or geometry. The sterilizing and/or treatment procedures are accomplished with one or more sterilization cycles.

In order to insure sufficient sterilization or treatment when only a discrete amount of gas is introduced, the apparatus 6 includes a controller for controlling a repeating sterilization cycle. The controller separately and repeatedly actuates the vacuum, the gas injection, the radio frequency energy, and the exhausting of spent gases. In this way, the articles or substrates within the sterilization or treatment chamber are continually subjected to a series of uniformly distributed gas plasma.

The controller can be any controller capable of separately actuating the vacuum pump 40, the gas injection valve 34, actuation of the generator source 22, and the exhaustion of gases through the exhaust port 42 in a systematic and controlled manner. An exemplary controller for controlling a sterilization or treatment cycle as just described is illustrated in FIGS. 2 and 3. The controller includes a rotating chopper valve 44 that is rotated by a chopper valve drive motor 46. A top view of the chopper valve 44 is shown in FIG. 3. The chopper valve 44 includes an orifice 46 that is alignable with the exhaust port 42. As the chopper valve 44 rotates, the orifice 46 passes in and out of alignment with exhaust port 42. The vacuum pump 40 is continuously actuated so that a vacuum will be applied to the reaction chamber 14 as the orifice 46 becomes aligned with the exhaust port 42. Disposed on the chopper valve 44 are a series of indicators which can be sensed by a sensor, such as an optical sensor (not shown), and used to actuate the gas injection valve 34 and the generator source 22. A gas injection indicator 48 is provided for actuating the valve 34 to inject a gas through the gas injection port 24. Spaced-apart from the gas injection indicator 48 is a radio frequency "on" indicator 50. As the radio frequency "on" indicator passes the sensor, a signal is sent to actuate the radio frequency generator source 22. The radio frequency energy source 22 remains actuated until the sensor senses a radio frequency "off" indicator 52.

The sensor will preferably be connected to a microprocessor or other controller for sending signals to actuate the generator source 22 and the gas injection valve 34 so that gas can be injected and radio frequency energy can be applied at the appropriate times.

In this way, the chopper valve 44 acts as an event timer which controls a sterilization or treatment cycle capable of producing a series of uniformly distributed plasma treatments within the reaction chamber 14, regardless of its size or geometry. As the chopper valve 44 rotates, the orifice 46 comes into alignment with the exhaust port 42 thereby creating a vacuum within the chamber 14. As the orifice 46 passes out of alignment, the vacuum is stopped and a static condition is allowed to develop within the chamber 14. At this point, the sensor senses the gas injector indicator 48 which sends a signal to open the valve 34 and to inject gas into the reaction chamber 14 through the gas injection port 24. Because of the static condition within the chamber 14, the gas uniformly distributes itself throughout the reaction chamber 14. The sensor then senses the radio frequency "on" indicator and a signal is sent to the radio frequency generator source 22 to apply radio frequency energy to the gas and to produce a uniformly distributed gas plasma which reacts with the microorganisms on the articles or otherwise treats the substrates. The sensor then senses the radio frequency "off" indicator 52 and sends a signal to cease application of the radio frequency energy. The orifice 46 then comes back into alignment with the exhaust port 42 to exhaust the spent gases and to again create a vacuum within the chamber 14. The cycle is then repeated as often as necessary until the sterilization or treatment procedure is complete. The repetition rate of the cycle is a function of the rotational speed of the chopper valve 44, and the duration of any given event in the cycle is a function of the placement of the indicators 48–52 on the chopper valve 44. Preferably, the cycle will be repeatable up to about 100 cycles per minute. Although the controller for controlling the sterilization or treatment cycle of the apparatus 6 has been described in connection with the chopper valve 44, any controller capable of separately actuating the events in the cycle can be employed. For example, a personal computer could be configured to sequentially actuate the pump 44, the injection valve 34, and the generator source 22.

The invention further provides a method and apparatus for sterilizing articles that are prepackaged in a container. When articles are manufactured, it is desirable to deliver them to the end user in a sterile protective package. This may require sterilizing the articles and then packaging them in a sterile environment. This invention eliminates such a procedure by sterilizing the articles while within their packaging materials. To sterilize the articles in this manner, the invention employs a packaging container for prepackaging the articles. The container is constructed of a material transparent to electromagnetic radiation frequency energy, such as plastic. The articles are placed in the container, and before the container is sealed the container is pumped to a vacuum of about 1 mTorr to 100 mTorr. The container is then back-filled with water vapor to a pressure of about 100 mTorr to 100 Torr. To back-fill the water vapor, a carrier gas is employed. The carrier gas is preferably air, but other gases can be employed such as argon, hydrogen, nitrogen, oxygen, helium, nitrogen tri-fluoride, nitrous oxide or mixtures thereof.

The prepackaged articles are then sterilized by placing the container in close proximity to an electromagnetic radiation source. The energy source is activated for a predetermined time to form a highly energetic water vapor. The electromagnetic radiation energy is then ceased for a predetermined time so that a static condition can develop within the container. This allows the pressure to become equalized and the concentration of the gases to become uniform throughout the volume of the container. The electromagnetic radiation energy is then reactivated to produce a uniformly distributed plasma. The energy source remains on for a predetermined time and the cycle may be repeated as many times as needed to complete the sterilization process. During the process the reactive radicals in the plasma vaporize and combine with the by-products of spores or other microorganisms on the articles. This produces water vapor, oxygen, nitrogen, and small amounts of carbon dioxide and carbon monoxide which all remain in the package until opened. However, the combination of these gases is inert and can be safely exhausted into the atmosphere when the containers are opened. In this way, the articles in the container remain sterilized until they are removed for use.

Although the foregoing invention has been described in detail by way of illustration and example, for purposes of clarity of understanding, it will be obvious that certain changes and modifications may be practiced within the scope of the appended claims.

What is claimed is:

1. A method for treating substrates, comprising:

(a) placing at least one substrate into a chamber;

(b) applying a vacuum to the chamber;

(c) ceasing application of the vacuum and allowing a static condition to develop in the chamber where the pressure throughout the chamber is essentially equal and constant;

(d) after the static condition has developed, introducing an amount of gas into the chamber and allowing the gas to uniformly distribute throughout the chamber; and (e) applying electromagnetic radiation energy to the chamber after the gas has become uniformly distributed within the chamber to produce a substantially uniformly distributed plasma within the chamber.

2. The method of claim 1, further comprising:

(f) ceasing application of the electromagnetic radiation energy;

(g) exhausting gases from the chamber; and (h) repeating the steps (b) through (g).

3. The method of claim 1, wherein the substrate is selected from the group of substrates consisting of semiconductor substrates, microelectronic substrates, flat panel displays, and transducers.

4. The method of claim 1, wherein the plasma is produced to strip or clean the substrate.

5. The method of claim 1, wherein the plasma is produced to etch the substrate.

6. The method of claim 1, wherein the plasma is produced to deposit a substance on the substrate.

7. The method of claim 6, wherein the substance comprises a depositional film.

8. The method of claim 1, further comprising introducing a plurality of substrates into the chamber at the same time.

9. The method of claim 1, wherein the substrate has an area that is greater than about 400 mm by 400 mm.

10. The method of claim 1, wherein the gas is selected from the group of gases consisting of water vapor, $O_2$, NO, $N_2O$, air, and hydrogen peroxide.

11. The method of claim 10, wherein the water vapor is introduced into the chamber with a carrier gas.

12. The method of claim 11, wherein the carrier gas is selected from the group consisting of air, argon, oxygen, nitrogen, helium, nitrous oxide and nitrogen tri-fluoride.

13. The method of claim 1, wherein the electromagnetic radiation energy is in the range from about 5 KHz to 10 GHz.

14. The method of claim 13, wherein the electromagnetic radiation energy is about 2.45 GHz.

15. The method of claim 1, wherein the pressure within the chamber when the gas is introduced is in the range from about 0.01 Torr to 100 Torr, and wherein the temperature within the chamber is in the range from about 25° C. to 1000° C.

16. A method for treating substrates, comprising:

placing at least one substrate into a chamber;

applying a vacuum to the chamber;

introducing only water vapor into the chamber; and applying electromagnetic radiation energy to the chamber to produce a substantially uniformly distributed plasma within the chamber.

* * * * *